United States Patent [19]

Maclaren et al.

[11] Patent Number: 5,376,533
[45] Date of Patent: Dec. 27, 1994

[54] METHODS AND COMPOSITIONS FOR THE DETECTION OF ADDISON'S DISEASE

[75] Inventors: Noel K. Maclaren, Archer; Yao H. Song, Gainesville, both of Fla.

[73] Assignee: University of Florida, Gainesville, Fla.

[21] Appl. No.: 66,281

[22] Filed: May 24, 1993

[51] Int. Cl.5 ............................................ G01N 33/573
[52] U.S. Cl. ...................................... 435/7.4; 435/18; 436/506; 436/811
[58] Field of Search .......................... 435/7.1, 7.4, 18; 436/506, 811

[56] References Cited

FOREIGN PATENT DOCUMENTS 2256046 11/1992 United Kingdom.

OTHER PUBLICATIONS

Picado–Leonard et al., Cloning and Sequence of the Human Gene for P450c17 (Steroid 17α–Hydroxylase/17,20 Lyase): Similarity with the Gene for P450c21. DNA 6(5): 439–448, 1987.

Bednarek, J., J. Furmaniak, N. Wedlock, Y. Kiso, A. Baumann–Anticzak, S. Fowler, H. Krishnan, J. A. Craft, and B. Rees Smith (1992) "Steroid 21–hydroxylase is a major autoantigen involved in adult onset autoimmune Addison's disease" FEBS 309(1):51–55.

Winqvist, Ola, F. Anders Karlsson, and Olle Kampe (1992) "21–hydroxylase, a major autoantigen in idiopathic Addison's disease" The Lancet 339:1559–1562.

Krohn, Kai, Raivo Uibo, Einari Aavik, Park Peterson, and Katja Savilahti (1992) "Identification by molecular cloning of an autoantigen associated with Addison's disease as steroid 17α–hydroxylase" The Lancet 339:770–773.

Maclaren, Noel K., and William J. Riley (1986) "Inherited Susceptibility to Autoimmune Addison's Disease Is Linked to Human Leukocyte Antigens–DR3 and/or DR4, except when Associated with Type 1 Autoimmune Polyglandular Syndrome" Journal of Clinical Endocrinology and Metabolism 62(3):455–459.

Neufeld, Michel, Noel K. Maclaren, and Robert M. Blizzard (1981) "Two Types of Autoimmune Addison's Disease Associated with Different Polyglandular Autoimmune (PGA) Syndromes" Medicine 60(5):355–362.

Davenport, John, Charles Kellerman, David Reiss, and Lawrence Harrison (1991) "Addison's Disease" AFP 43(4):1338–1342.

Oelkers, W., S. Diederich, and V. Bahr (1992) "Diagnosis and Therapy Surveillance in Addison's Disease: Rapid Adrenocorticotropin (ACTH) Test and Measurement of Plasma ACTH, Renin Activity and Aldosterone" Journal of Clinical Endocrinology and Metabolism 75(1):259–264.

Freeman, M., and A. P. Weetman (1992) "T and B cell reactivity to adrenal antigens in autoimmune Addison's disease" Clin. exp. Immunol. 88:275–279.

*Primary Examiner*—Toni R. Scheiner
*Assistant Examiner*—Donna C. Wortman
*Attorney, Agent, or Firm*—Saliwanchik & Saliwanchik

[57] ABSTRACT

An epitope of 21-hydroxylase has been identified which specifically reacts with autoantibodies to 21-hydroxylase. This epitope immunoreacts with anti-adrenocortical autoantibodies characteristically present in patients having autoimmune Addison's disease. The peptide can be used in a specific, sensitive immunoassay for the detection of these autoantibodies in the diagnosis of Addison's disease. The immunoassay permits the diagnosis of autoimmune Addison's disease and has considerable value in the screening of persons at risk. Persons in the early phases or at clinical onset of any kind of adrenocortical disease can also be screened to exclude Addison's disease as a cause.

2 Claims, 1 Drawing Sheet

METHODS AND COMPOSITIONS FOR THE DETECTION OF ADDISON'S DISEASE

BACKGROUND OF THE INVENTION

The adrenal glands secrete steroid hormones such as cortisol which are essential to life. Victims of Addison's disease suffer from lymphocytic infiltration and the subsequent destruction of these important glands. The initial symptoms of Addison's disease are subtle, consisting of such features as muscular weakness and increased pigmentation of the skin. As the disease progresses, unexplained dehydration, low blood pressure, and disturbances in blood electrolytes become manifest. Once the adrenal glands fail completely, life is not possible without specific hormone replacement treatment. However, if the disease is correctly diagnosed, the affected patient can live a normal life by taking replacement quantities of steroid hormones most usually as daily pills. Family members of patients with Addison's disease are also prone to the disease. Since the treatment of this otherwise fatal disease can so readily restore health and bodily functions, the identification of patients or their family members with impending disease is important to the appropriate treatment of the condition.

Addison's disease is probably much more common than the limited number of prevalence studies available would suggest. The most famous American with the disease was the late President John F. Kennedy, albeit his affliction was a well-kept secret for most of his life. He was diagnosed after a classical presentation of the disease at age 30, while he was returning through London from a visit to Ireland, only one year after being elected to the U.S. House of Representatives. Within three years he was established on steroid replacement therapies of 25 mg of cortisone and the intermittent implantation of 150 mg DOCA pellets. Throughout the years, his appearance changed dramatically from a gaunt congressman with Addison's disease to that of a heavy set and jowly senator and president on steroid therapy. As a senator, he successfully underwent back surgery after his diagnosis of adrenocortical failure in 1955, an event which was published in JAMA Archive of Surgery although he was not identified as the patient until a follow-up article in JAMA in 1967 (Blair, Jr., C., J. Blair [1976] The Search for JFK, Berkley Publishing Corp., New York, pp. 560-579).

There are many causes of Addison's disease; however, two of the most important are tuberculosis infections and autoimmunity. The treatment for Addison's disease depends upon the cause. Tuberculosis-generated Addison's disease is treated by chemotherapy to eliminate the microorganism. In the case of autoimmune Addison's, however, it is the host's own immune system that destroys the host's adrenal gland. Therefore, treatment of this form of the disease can involve immunomodulation.

In autoimmune Addison's disease, there is loss of cells of the adrenal cortex but not of the medulla. The adrenal cortex is arranged anatomically into 3 zones, each with distinct, albeit overlapping, properties and functions. Adjacent to the fibrous capsule is found the zona glomerulosa, characterized by nests of cells involved in the secretion of steroid hormones that promote sodium retention and potassium excretion. The most powerful of these hormones is aldosterone. Moving into the gland, the zona faciculata is next encountered. Here, columns of epithelial cells secrete quantities of the glucocorticoid hormones, principally cortisol. Glucocorticoid hormones have powerful metabolic action promoting breakdown of body protein stores and enhancing hepatic gluconeogenesis, thus raising blood glucose levels when found in excess. The innermost zone has cells distributed in a reticular pattern which secrete the 17-hydroxylated sex hormones, principally dihydroepiandrosterone. All three zones become destroyed by the disease. The adrenal medulla is spared in autoimmune Addison's disease and is an organ for the production and secretion of catecholamines.

Autoimmune Addison's disease often occurs together with other autoimmune endocrinopathies. This phenomenon has been termed autoimmune polyglandular disease or APS (Neufeld et al. [1981] Medicine 60:718-723). In type 1 APS, patients are often affected by several component problems, including hypoparathyroidism, hypogonadism, pernicious anemia, and chronic active hepatitis. Patients also often have underlying defects in cellular immunity leading to chronic muco-cutaneous moniliasis. In the more common APS, type 2, Addison's disease is associated with chronic lymphocytic thyroiditis (Hashimoto's disease, but sometimes Graves' disease), insulin dependent diabetes (IDD), and pernicious anemia. In type 1 APS there are no genetic associations with human leukocyte antigens (HLA); however, predisposition to type 2 disease is strongly linked to the HLD-DR locus, and particularly to the DR3 and DR4 alleles (Maclaren et al. [1986] J. Clin. Endo. Metab. 62:455-459). Addison's disease occurring in both contexts is associated with circulating autoantibodies to the adrenal cortex, which are detectable by indirect immunofluorescence of sections of frozen human adrenal glands.

The adrenocortical autoantibodies of the disease sometimes react to steroid hormone secreting cells in non-adrenal sites such as the granulosa/luteal portion of the graafian follicles of the ovary, the Leydig cells of the testes, and the syncytiotrophoblast of the placenta. Therefore, some patients can have both the common adrenal gland-specific antibody as well as the steroidal cell autoantibody (Elder and Maclaren [1981] J. Clin. Endocrinol. Metab. 52:143-148). These patients are only those patients afflicted with type 1 APS. Patients with type 2 APS only have adrenal specific antibodies.

Recently, several papers have reported serum reactivity to p450 enzymes in patients with type 1 APS. One paper describes reactivity with the 17-hydroxylase enzyme (Krohn et al. [1992] Lancet 339:770-773); the others describe reactivity to the 21-hydroxylase enzyme (Winquist et al. [1992] Lancet 339:1559-1562; Bednarek et al. [1992] FEBS Lett. (Netherlands) 309:(1):51-55). These two enzymes are important to steroidogenesis. Each enzyme is 55 kDa. Neither of these enzymes are targeted by other autoimmune endocrinopathies.

The enzyme 21-hydroxylase promotes the conversion of pregnenalone to progesterone in the chemical pathways for steroid hormone formation. The enzyme has been described in U.K. Patent Application GB 2 256 046 for use in methods and kits for detecting adrenal autoantibodies. Others have suggested inconsistency of results in using various immunological tests for the detection of Addison's disease (Freeman, M., P. Weetman [1992] Clin. Exp. Immunol. 88(2):275-279). At present, diagnosis and therapy surveillance of Addison's disease are carried out by the nonspecific rapid adrenocorticotropin hormone (ACTH) test (Oelkers et al.

[1992] J. Clin. Endocrinol. Metab. 75(1):259–264; Davenport et al. [1991] Am. Faro. Physician 43(4):1338–1342).

BRIEF SUMMARY OF THE INVENTION

The subject invention pertains to fragments of 21-hydroxylase with which antibodies to 21-hydroxylase specifically immunoreact. A further aspect of the invention is specific, sensitive immunoassays for the detection of autoantibodies associated with Addison's disease. The immunoassays of the subject invention permit the diagnosis of autoimmune adrenal disease, and have considerable value in the screening of persons at risk, as well as persons in the early phases of the disease or at clinical onset of the disease when other causes of adrenocortical disease can be excluded. The screening of patients and their family members for adrenocortical autoantibodies can identify those at risk for this potentially fatal disease.

Six cDNA fragments of the 21-hydroxylase were amplified by PCR from human adrenal cDNA. The PCR amplified fragments were cloned into an expression plasmid. Recombinant 21-hydroxylase fragments were expressed in *E. coli* and epitope mapping was performed using Western blotting. All six fragments reacted with a positive control sera (rabbit anti-21-hydroxylase). Serum from patients with Addison's disease was tested. Autoantibodies from the patient sera were found to react with the middle portion of 21-hydroxylase (B fragment, AA 164-356). The B fragment was further divided into 3 small overlapping fragments (D E, F). The greatest reactivity was with the E fragment (AA 272-356). No positive binding was found in the negative control human sera tested.

BRIEF DESCRIPTION OF THE SEQUENCES

Figure 1:
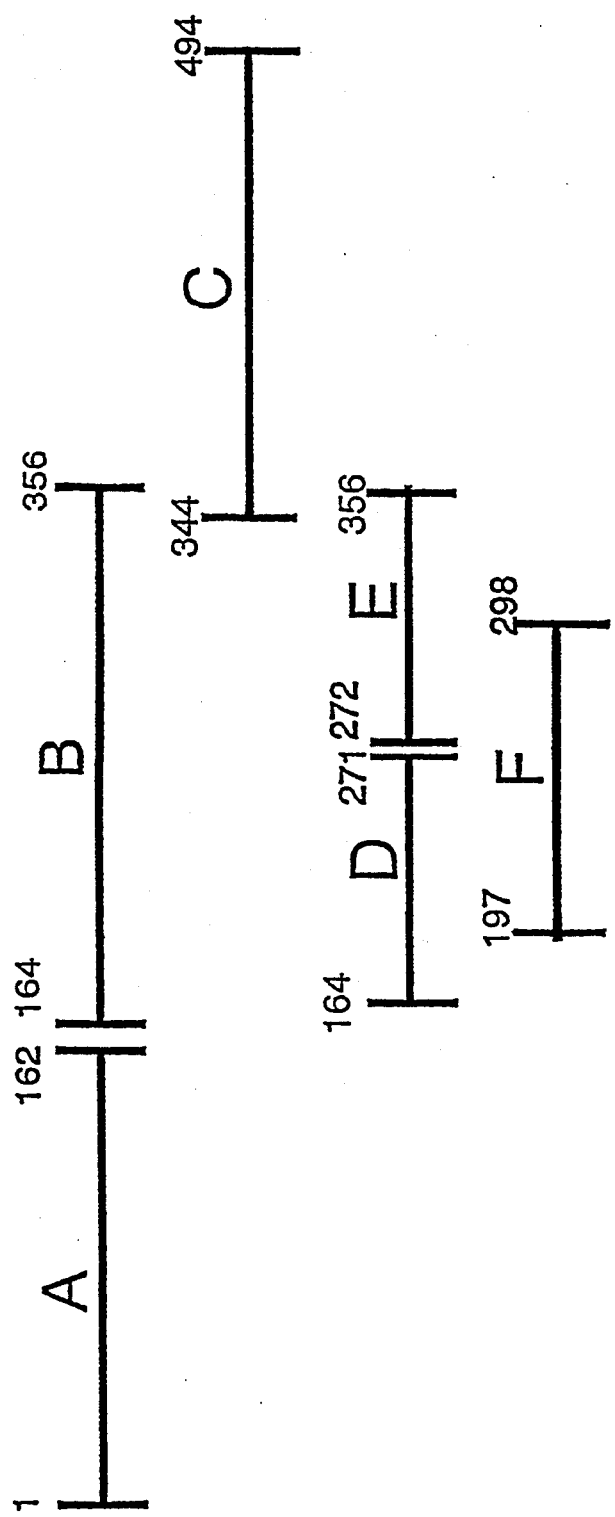
FIG. 1 shows a schematic representation of fragments A-F of the 21-hydroxylase enzyme molecule.

SEQ ID NO. 1 is a forward primer used according to the subject invention.

SEQ ID NO. 2 is a reverse primer used according to the subject invention.

SEQ ID NO. 3 is a forward primer used according to the subject invention.

SEQ ID NO. 4 is a reverse primer used according to the subject invention.

SEQ ID NO. 5 is a forward primer used according to the subject invention.

SEQ ID NO. 6 is a reverse primer used according to the subject invention.

SEQ ID NO. 7 is a forward primer used according to the subject invention.

SEQ ID NO. 8 is a reverse primer used according to the subject invention.

SEQ ID NO. 9 is a forward primer used according to the subject invention.

SEQ ID NO. 10 is a reverse primer used according to the subject invention.

SEQ ID NO. 11 is a forward primer used according to the subject invention.

SEQ ID NO. 12 is a reverse primer used according to the subject invention.

DETAILED DISCLOSURE OF THE INVENTION

The subject invention concerns the development of a test to detect autoantibodies in persons who have developed, or are at risk of developing, autoimmune Addison's disease. Addison's disease is characterized by the immunological destruction of the adrenal glands by these autoantibodies. The immunological process attacks 21-hydroxylase, an enzyme which is important to normal steroidogenesis.

A specific aspect of the current invention is fragments of the 21-hydroxylase molecule which react to the autoantibody to 21-hydroxylase. One embodiment of the invention comprises a fragment of amino acids 164-356 of the 21-hydroxylase enzyme. Another embodiment of the invention comprises a fragment of amino acids 272-356. A further embodiment of the invention comprises a fragment of a highly conserved portion of the 21-hydroxylase enzyme of amino acids 338-360. The amino acid designations provided herein correspond to the well known sequence for 21-hydroxylase, as found, for example, in White et al. [1986] Proc. Natl. Acad. Sci. USA 83 at 5113.

The fragments described herein can be used to detect the presence of the 21-hydroxylase autoantibody in a patient's serum. These fragments contain the immunological reactivity of the molecule and can be used in highly specific diagnostic assays to identify the autoantibody associated with Addison's disease. Detection of the autoantibody in patients with the disease helps to exclude other possible causes of the disease, such as a tuberculosis infection. Further, the identification of the antibody in persons with symptoms suggestive of possible disease or those at increased risk of the disease because of having another immunological glandular failure, such as insulin dependent diabetes or having family members with Addison's disease, will permit the early diagnosis of impending Addison's disease and its early treatment.

In one embodiment of the subject invention, the test developed using the peptide of the subject invention is used to identify newly diagnosed Addison's patients having the autoimmune form of the disease. The clinical value of this is two-fold. Patients with autoimmune Addison's disease will not be identified as having Addison's caused by fungal and tuberculosis infections. Tuberculosis is a serious disease which is on the rise as a direct consequence of the AIDS epidemic. The diagnosis of tuberculosis necessitates prolonged antibiotic therapy. The assay identifies only patients suffering from the autoimmune form of the disease and eliminates AIDS as an underlying cause of the disease. Patients identified with autoimmune Addison's should be studied clinically for associated immunological disorders, especially those diseases in type 2 APS. Further, apparently unaffected family members should be tested for the autoantibody since the disease is more common among relatives of victims and can be life-threatening unless the disease is recognized and specifically treated by daily replacement of steroid hormones.

Patients with autoimmune endocrinopathies such as insulin dependent diabetes are unusually prone to develop autoimmune Addison's disease and should, therefore, be screened for the autoantibody (Maclaren et al. [1982] Pediatric Annals 11:333–347; Riley, Maclaren et al. [1980] J. Pediatr. 97:191–194). Those patients found positive for the autoantibody should be considered for close monitoring by hormonal analyses including determination of ACTH, renin, aldosterone, and cortisol levels or treated prophylactically by steroid hormone replacement therapy (Ketchum, Maclaren et al. [1984] J. Clin. Endo. Metab. 58:1166–1170). Patients with Graves' disease or Hashimoto's disease and/or pernicious anemia and vitiligo, especially if extensive, should be screened for the autoantibody, as should their unaffected family members. The reliable immunological assay of the subject invention, which can be automated, or developed as a finger stick screening test readily performed in a physician's office, makes it possible for all persons to be routinely tested for this lethal condition which can be readily treated by steroid hormone replacement therapy.

Smaller portions and variants of the claimed peptides which retain the immunological reactivity of the exemplified peptides are within the scope of the subject invention. Also, because of the redundancy of the genetic code, a variety of different DNA sequences can encode the peptides disclosed herein. It is well within the skill of a person trained in the art to create these alternative DNA sequences encoding the same, or essentially the same, peptides. These variant DNA sequences are within the scope of the subject invention. As used herein, reference to "essentially the same" sequence refers to sequences which have amino acid substitutions, deletions, additions, or insertions which do not materially affect immunological reactivity with the 21-hydroxylase autoantibody.

As a person skilled in the art would appreciate, certain amino acid substitutions within the amino acid sequence of the peptide are acceptable and can be readily made if these substitutions are in regions which are not critical to immunological reactivity. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the immunological reactivity of the compound with autoantibodies to 21-hydroxylase. Table 1 provides a listing of examples of amino acids belonging to each class.

TABLE 1

| Class of Amino Acid | Examples of Amino Acids |
| --- | --- |
| Nonpolar | Ala, Vah Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the immunological reactivity of the peptides.

MATERIALS AND METHODS

Serum was obtained from persons with isolated Addison's disease or type II APS who had adrenal autoantibodies detectable by indirect immunofluorescence on human adrenal cryo-cut sections. Negative control sera was collected from persons without any organ-specific autoantibodies. Positive control sera was collected from rabbits immunized with purified 21-hydroxylase.

A human adrenal cDNA library was created using the mRNA extracted from human adrenal gland, and cDNA fragments were amplified by PCR using synthetic DNA primers (SEQ ID NOS. 1-12). As would be appreciated by one skilled in the art, these primers have been optimized for this particular use and, therefore, may not correspond directly to the DNA sequences known for the 21-hydroxylase gene. For example, all forward primers contain the restriction site for BamHi, and all reverse primers contain the restriction site for EcoRI. The sites allow the amplified fragments to be cloned. The primers used for each fragment are shown in Table 2.

TABLE 2

Primers for preparing fragments of 21-hydroxylase

Fragment A
Forward: GCGTGGATCC ATGCTGCTCC TGGGCCTGCT G (SEQ ID NO. 1)
Reverse: GAGAGAATTC CTCCTCAATG GCCACAGGGG T (SEQ ID NO. 2)

Fragment B
Forward: GGAGGGATCC TCTCTCCTCA CCTGCAGCAT C (SEQ ID NO. 3)
Reverse: GCACGAATTC CCGCAGGCGC AGCACCTCGG C (SEQ ID NO. 4)

Fragment C
Forward: ACGGGGATCC TTGCTCAATG CCACCATCGC C (SEQ ID NO. 5)
Reverse: TCCTGAATTC TCACTGGTTC TGGCCCGGGC T (SEQ ID NO. 6)

Fragment D
Forward: GGAGGGATCC TCTCTCCTCA CCTGCAGCAT C (SEQ ID NO. 7)
Reverse: GTCCGAATTC CTCTTCCATG CTCGGCTGCG C (SEQ ID NO. 8)

Fragment E
Forward: CATGGGATCC GGCTCTGGAC AGCTCCTGGA A (SEQ ID NO. 9)
Reverse: GCACGAATTC CCGCAGGCGC AGCACCTCGG C (SEQ ID NO. 10)

Fragment F
Forward: GGTGGGATCC ACCTGGAGCC ACTGGTCCAT C (SEQ ID NO. 11)
Reverse: AGGAGAATTC GTTTGCTGTG GTCTCAGTGC C (SEQ ID NO. 12)

The PCR-amplified fragments were cloned into an expression plasmid (pGEX2T). Recombinant 21-hydroxylase fragments were expressed in E. coli as fusion proteins with glutathione S-transferase.

Recombinant fragments A, B, and C encompassed the entire 21-hydroxylase enzyme gene. The B fragment was also expressed as 3 overlapping component fragments (D, E, F) to further map the domain. Recombinant fragments A-F comprise the amino acids as listed in Table 3.

TABLE 3

| Fragment | Amino Acids |
| --- | --- |
| A | 1-162 |
| B | 164-356 |
| c | 344-494 |
| D | 164-271 |
| E | 272-356 |
| F | 197-298 |

Also of interest is a conserved region of the 21-hydroxylase enzyme from amino acid 338 to 360.

Epitope mapping was performed by Western blotting. E. coli extracts containing recombinant proteins were solubilized in SDS gel loading buffer after reduction by DTT and heating for 3 minutes at 100° C. before loading. After separation by SDS-PAGE, the proteins were immunoblotted onto Immobilon-P membranes. Strips of the membranes were cut and incubated with 1% BSA in TBST to block free potential binding sites. Test sera at 1/100 dilutions were incubated with the antigen-containing strips. Strips were then incubated with an anti-human polyvalent immunoglobulin alkaline phosphatase conjugate to detect those sera containing autoantibody and reacting with the antigen. An anti-rabbit conjugate was used for the positive control antisera that had been developed in rabbits.

Following are examples which illustrate procedures, including the best mode, for practicing the invention. These examples should not be construed as limiting.

EXAMPLE 1

Thirty serum samples from persons with isolated Addison's or type 2 APS confirmed by the presence of detectable autoantibodies on human adrenal cryo-cut section and twenty control samples were epitope mapped by Western blot analysis. Twenty-six of thirty (87%) of the patients' sera reacted with 21-hydroxylase. Of the 6 cDNA fragments of 21-hydroxylase (A-F), maximal reactivity (83%) was to the B fragment (AA 164-356). For this fragment, most of the reactivity (>50%) was confined to the E fragment (AA 272-356). Recombinant B fragment (AA 164-356), was used to preabsorb sera reactive to the B fragment by Western blotting. All reactivity diminished, but only one serum was completely quenched.

To prove the specificity of the autoantibody responses to the 21-hydroxylase enzyme, four steroid hormone synthesis enzymes were expressed and contacted with sera from patients with Addison's disease. These enzymes are 11-$\beta$-hydroxylase, p450scc, 17-$\alpha$-hydroxylase, and 3-$\beta$-hydroxysteroid dehydrogenase proteins. No sera reacted to any of these enzymes. These findings demonstrate the specificity of the diagnostic tests of the subject invention in detecting autoantibodies to the 21-hydroxylase enzyme.

EXAMPLE 2

Methods of Detecting Autoantibodies Associated with Autoimmune Addison's Disease The peptides of the subject invention may be used in a number of standard immunological methods to diagnose the presence of Addison's disease. Generalized procedures for immunological methods which include enzyme linked immunosorbent assay (ELISA) and radioimmunoassay (RIA) are well known to those skilled in the art. In an ELISA procedure, the peptides of the subject invention would be coated onto a solid substrate and then contacted with sera of a patient suspected of having autoimmune Addison's disease. This contacting is done under conditions which will promote antigen-/antibody immunocomplex formation between antigens and antibodies present in the sample. The autoantibodies in the sera would bind to the claimed peptides, forming an antigen/antibody complex. The resulting immunocomplex can be readily detected utilizing standard labeling procedures. For example, autoantibody binding may be visualized by contacting the antigen/antibody complex with a labelled antibody to the autoantibody. It would be apparent to one skilled in the art that there are numerous variations to this procedure.

EXAMPLE 3

Kits for Assay of Autoantibodies Associated with Autoimmune Addison's Disease

A reagent kit can be provided which facilitates convenient analysis of sera samples using the novel peptides of the subject invention. Kits can be prepared which utilize recombinant or a synthetically produced peptides to serve as an antigen for the autoantibodies. The principles and methods for ELISA and RIA technologies to detect antibodies are well-established.

As an example, for the ELISA assay, one such kit could comprise the following components:

1. One or more of the peptides of the subject invention;
2. Enzyme (e.g., peroxidase);
3. Conjugated animal anti-human immunoglobulin; and
4. Positive and negative controls.

The above kit could be modified to include 96 well plastic plates, colorimetric reagents, ELISA readers, blocking reagents, and wash buffers.

Also by way of example, for the RIA, one such kit could comprise the following components:

1. One or more of the peptides of the subject invention;
2. Wash buffers;
3. Polyethylene glycol;
4. Goat or sheep antihuman precipitating (second) antibodies; and
5. Positive and negative controls.

Either of the above kits may be modified to include any appropriate laboratory supplies.

It should be understood that the examples and embodiments described herein are for illustrative purposes only and that various modifications or changes in light thereof will be suggested to persons skilled in the art and are to be included within the spirit and purview of this application and the scope of the appended claims.

---

We claim:

1. A method to aid in the diagnosis or detection of Addison's disease in a person having, or at risk for developing, Addison's disease, said method comprising contacting a sample of serum from said person with a peptide fragment of 21-hydroxlase, wherein said peptide fragment is selected from the group consisting of 21-hydroxylase amino acid 164 to amino acid 356, 21-hydroxylase amino acid 272 to amino acid 356, and 21-hydroxylase amino acid 338 to amino acid 360, and detecting binding of said peptide fragment and autoantibodies present in said sample, wherein the presence of said binding indicates that said person may have or be at risk for developing Addison's disease.

2. A kit for use in a method to aid in the diagnosis or detection of Addison's disease, said kit comprising
   a) a peptide fragment of 21-hydroxylase, wherein said peptide fragment is selected from the group consisting of amino acid 164 to amino acid 356, amino acid 272 to amino acid 356, and amino acid 338 to amino acid 360 of said 21-hydroxylase; and
   b) animal anti-human immunoglobulin.

* * * * *

UNITED STATES PATENT AND TRADEMARK OFFICE
CERTIFICATE OF CORRECTION

PATENT NO. : 5,376,533
DATED : December 27, 1994
INVENTOR(S) : Noel K. Maclaren, et al.

It is certified that error appears in the above-indentified patent and that said Letters Patent is hereby corrected as shown below:

Column 2, line 58:   Delete "pregnenalone" and insert --pregenalone--.

Column 3, line 2:    Delete "Am. Faro." and insert --Am. Fam.--.

Column 6, line 20:   Delete "BamHi" and insert --BamHI--.

Column 6, line 60:   Delete "c" and insert --C--.

Column 13, line 14:  Delete "hydroxlase," and insert --hydroxylase,--.

Signed and Sealed this

Thirtieth Day of May, 1995

*Attest:*

BRUCE LEHMAN

*Attesting Officer*     Commissioner of Patents and Trademarks

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 31 bases
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:1:

GCGTGGATCC ATGCTGCTCC TGGGCCTGCT G                    31

( 2 ) INFORMATION FOR SEQ ID NO:2:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GAGAGAATTC CTCCTCAATG GCCACAGGGG T                    31

( 2 ) INFORMATION FOR SEQ ID NO:3:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

GGAGGGATCC TCTCTCCTCA CCTGCAGCAT C                    31

( 2 ) INFORMATION FOR SEQ ID NO:4:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

GCACGAATTC CCGCAGGCGC AGCACCTCGG C                    31

( 2 ) INFORMATION FOR SEQ ID NO:5:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

ACGGGGATCC TTGCTCAATG CCACCATCGC C                    31

( 2 ) INFORMATION FOR SEQ ID NO:6:

( i ) SEQUENCE CHARACTERISTICS:
        ( A ) LENGTH: 31 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

TCCTGAATTC TCACTGGTTC TGGCCCGGGC T                    31

-continued ( 2 ) INFORMATION FOR SEQ ID NO:7:

( i ) SEQUENCE CHARACTERISTICS:
　　　　　　　　( A ) LENGTH: 31 bases
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (synthetic)

( x i ) SEQUENCE DESCRIPTION: SEQ ID NO:7:

GGAGGGATCC TCTCTCCTCA CCTGCAGCAT C　　　　　　　　　　　　　　　　　　　　　　　31

( 2 ) INFORMATION FOR SEQ ID NO:8:

( i ) SEQUENCE CHARACTERISTICS:
　　　　　　　　( A ) LENGTH: 31 bases
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (synthetic)

( x i ) SEQUENCE DESCRIPTION: SEQ ID NO:8:

GTCCGAATTC CTCTTCCATG CTCGGCTGCG C　　　　　　　　　　　　　　　　　　　　　　　31

( 2 ) INFORMATION FOR SEQ ID NO:9:

( i ) SEQUENCE CHARACTERISTICS:
　　　　　　　　( A ) LENGTH: 31 bases
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (synthetic)

( x i ) SEQUENCE DESCRIPTION: SEQ ID NO:9:

CATGGGATCC GGCTCTGGAC AGCTCCTGGA A　　　　　　　　　　　　　　　　　　　　　　　31

( 2 ) INFORMATION FOR SEQ ID NO:10:

( i ) SEQUENCE CHARACTERISTICS:
　　　　　　　　( A ) LENGTH: 31 bases
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (synthetic)

( x i ) SEQUENCE DESCRIPTION: SEQ ID NO:10:

GCACGAATTC CCGCAGGCGC AGCACCTCGG C　　　　　　　　　　　　　　　　　　　　　　　31

( 2 ) INFORMATION FOR SEQ ID NO:11:

( i ) SEQUENCE CHARACTERISTICS:
　　　　　　　　( A ) LENGTH: 31 bases
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (synthetic)

( x i ) SEQUENCE DESCRIPTION: SEQ ID NO:11:

GGTGGGATCC ACCTGGAGCC ACTGGTCCAT C　　　　　　　　　　　　　　　　　　　　　　　31

( 2 ) INFORMATION FOR SEQ ID NO:12:

( i ) SEQUENCE CHARACTERISTICS:
　　　　　　　　( A ) LENGTH: 31 bases
　　　　　　　　( B ) TYPE: nucleic acid
　　　　　　　　( C ) STRANDEDNESS: single
　　　　　　　　( D ) TOPOLOGY: linear ( i i ) MOLECULE TYPE: DNA (synthetic)

( x i ) SEQUENCE DESCRIPTION: SEQ ID NO:12:

AGGAGAATTC GTTTGCTGTG GTCTCAGTGC C    31